United States Patent
Elrod et al.

(10) Patent No.: US 6,809,643 B1
(45) Date of Patent: Oct. 26, 2004

(54) HEALTH MONITORING SYSTEM FOR CAR SEAT

(75) Inventors: Susan Vinz Elrod, Huntsville, AL (US); Richard W. Dabney, Tanner, AL (US)

(73) Assignee: The United States of America as represented by the Administrator of the National Aeronautics and Space Administration, Washington, DC (US)

(*) Notice: Subject to any disclaimer, the term of this patent is extended or adjusted under 35 U.S.C. 154(b) by 102 days.

(21) Appl. No.: 10/392,487

(22) Filed: Mar. 18, 2003

(51) Int. Cl.$^7$ .............................. G08B 1/08
(52) U.S. Cl. .................. 340/539.1; 340/573.1; 701/45; 180/271; 280/735
(58) Field of Search .............. 340/539.1, 539.15–573.1, 340/576, 438; 701/45; 180/271; 280/735

(56) References Cited

U.S. PATENT DOCUMENTS

| | | |
|---|---|---|
| 5,581,234 A | 12/1996 | Emery et al. |
| 5,618,056 A | 4/1997 | Schoos et al. |
| 5,678,854 A | 10/1997 | Meister et al. |
| 5,711,574 A | 1/1998 | Barnes |
| 5,790,031 A | 8/1998 | Shelton et al. |
| 5,838,233 A | 11/1998 | Hawes et al. |
| 5,851,026 A | 12/1998 | Schoos et al. |
| 5,912,624 A * | 6/1999 | Howard, II ............ 340/632 |
| 5,914,660 A * | 6/1999 | Mesibov et al. ........ 340/573.7 |
| 5,941,560 A | 8/1999 | Wolfram |
| 6,195,008 B1 * | 2/2001 | Bader ................. 340/573.1 |
| 6,283,504 B1 | 9/2001 | Stanley et al. |
| 6,304,179 B1 | 10/2001 | Lotito et al. |
| 6,357,790 B1 | 3/2002 | Swann et al. |
| 6,393,348 B1 * | 5/2002 | Ziegler et al. ............ 701/45 |
| 6,402,240 B1 | 6/2002 | Toba et al. |

* cited by examiner

Primary Examiner—Daryl Pope
(74) Attorney, Agent, or Firm—James J. McGroary; Peter J. Van Bergen

(57) ABSTRACT

A health monitoring system for use with a child car seat has sensors mounted in the seat to monitor one or more health conditions of the seat's occupant. A processor monitors the sensor's signals and generates status signals related to the monitored conditions. A transmitter wirelessly transmits the status signals to a remotely located receiver. A signaling device coupled to the receiver produces at least one sensory (e.g., visual, audible, tactile) output based on the status signals.

12 Claims, 4 Drawing Sheets

US 6,809,643 B1

HEALTH MONITORING SYSTEM FOR CAR SEAT

ORIGIN OF THE INVENTION

The invention was made was made by employees of the United States Government and may be manufactured and used by or for the Government for governmental purposes without the payment of any royalties.

BACKGROUND OF THE INVENTION

1. Field of the Invention

This invention relates to systems for monitoring a child in a car seat. More specifically, the invention is a system that uses sensors to monitor a variety of health indicators for an infant or child sitting in a car seat and then transmits the health indicators wirelessly to a remote signaling device.

2. Description of the Related Art

Parents today lead increasingly complex and demanding lives. For example, in two parent families, both parents frequently work for a variety of reasons ranging from the need to keep up with cost-of-living increases to the need for both parents to feel fulfilled on a business/professional level. The complexities and demands increase dramatically for single parents whose numbers have increased significantly over the last twenty years. However, along with managing business lives, all parents must also maintain a family life for their children. As a result of all of the above, infants and young children today spend a lot of time being driven around in the family vehicle. Whether it is going to and from daycare, running errands, or just the parent's desire to have their child with them, children today can spend several hours a week in a car.

Parents want to be sure their children are comfortable and safe while traveling. Further, there are laws mandating the use of child safety seats in vehicles. Thus, a variety of infant car seats currently on the market are designed to reduce the risk of injury in the event of a collision with another vehicle. However, none of today's car seats offer a parent the opportunity to monitor physiological conditions of the child in the car seat. This becomes important given the complexities of day-to-day life that may require parents to bring a sick child in the car. In addition, the medical profession's ability to diagnose many early childhood health conditions or concerns may make it desirable to frequently monitor a child. Such monitoring is not possible when traveling in a car.

SUMMARY OF THE INVENTION

Accordingly, it is an object of the present invention to provide a health monitoring system for use with a car seat.

Another object of the present invention to provide a system that can monitor a variety of physiological conditions of a child in a car seat and provide a sensory detectable signal when one or more of the physiological conditions may be of concern.

Other objects and advantages of the present invention will become more obvious hereinafter in the specification and drawings.

In accordance with the present invention, a health monitoring system is provided for use with a child car seat. Sensors are mounted in a child car seat to monitor an occupant sitting therein in terms of at least one of respiratory rate, heart rate and body temperature of the occupant. A processor mounted to the child car seat and coupled to the sensors monitors sensor signals and generates status signals related to at least one of respiratory rate, heart rate and body temperature of the occupant. A transmitter mounted to the child car seat and coupled to the processor wirelessly transmits the status signals to a remotely located receiver. A signaling device coupled to the receiver produces at least one sensory (e.g., visual, audible, tactile) output based on the status signals. The signaling device can be mounted in the vehicle in which the child car seat is installed or can be worn by the driver of the vehicle.

BRIEF DESCRIPTION OF THE DRAWING(S)

Other objects, features and advantages of the present invention will become apparent upon reference to the following description of the preferred embodiments and to the drawings, wherein corresponding reference characters indicate corresponding parts throughout the several views of the drawings and wherein.

DESCRIPTION OF THE PREFERRED EMBODIMENT(S)

Figure 1:
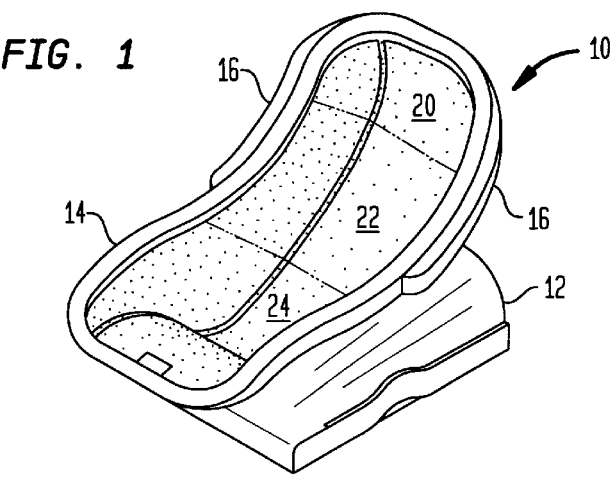
FIG. 1 is a perspective view of a conventional child car seat.

Referring now to the drawings, and more particularly to FIG. 1, a conventional child car seat is shown and referenced generally by numeral 10. Car seat 10 is representative of a well known car seat design having a base 12 that is typically attached to a vehicle's seat by means of a vehicle seat belt (not shown). A removable seat 14 is locked/unlocked to base 12 with the locking and unlocking operation typically controlled by means of a pull down handle 16 shown in its upright (locked) position. Handle 16 is pivoted over seat 14 to unlock same from base 12 and serve as a carrying handle for seat 14. Car seat 10 is generally used for newborns and children up to about 2 years old depending on their size and weight. Car seat 10 is designed to face rearward in a vehicle for very young children and forward when they are a little older.

It is to be understood that the present invention is in no way limited by the design of car seat 10 and that the present invention can be incorporated into any type of car seat (e.g., one piece, two piece as just described, etc.). However, since parental concerns about a child's welfare are most heightened when the child is very young (i.e., 0 to 2 years old), and since the very young child can be uncontrollably loud or fussy when they are uncomfortable, the description of the present invention will be referenced to car seat 10.

Figure 2:
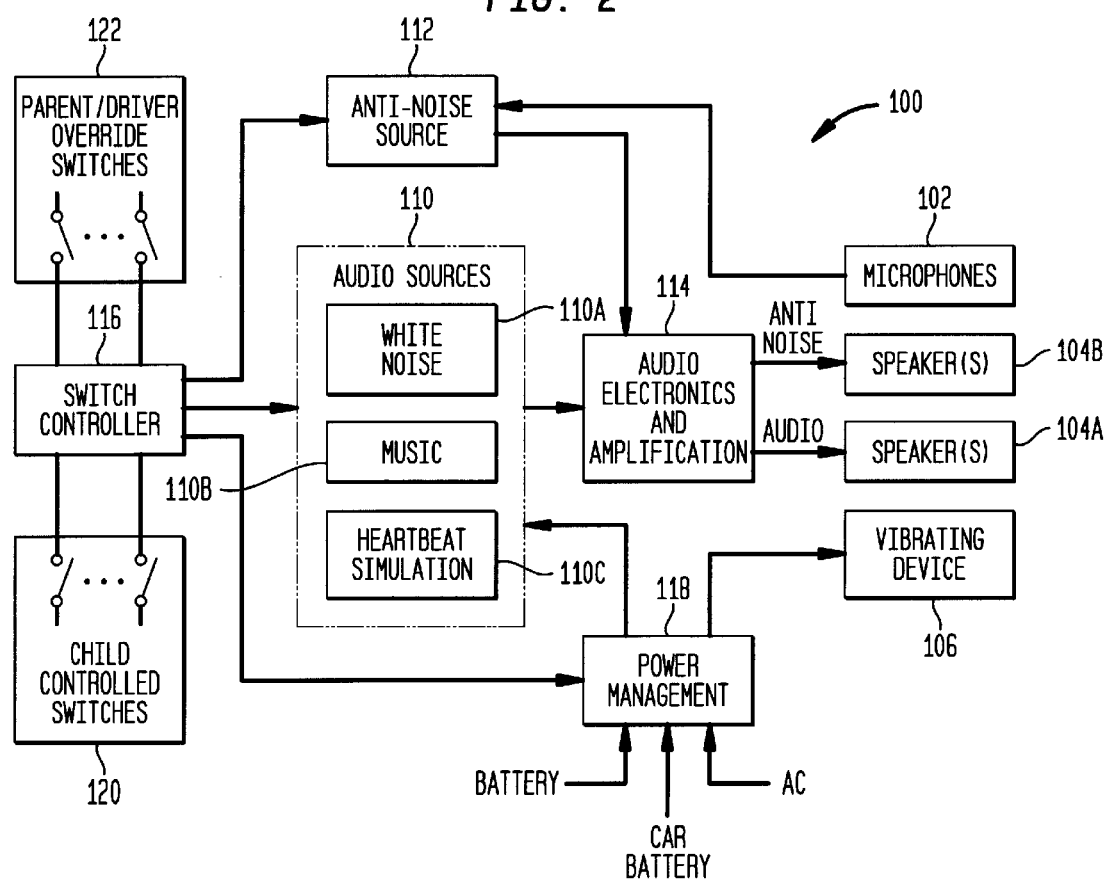
FIG. 2 is a schematic view of an entertainment and pacification system of the present invention that is to be used with a child car seat.

Referring additionally now to FIG. 2, an entertainment and pacification (E/P) system that it is to be used with car seat 10 is shown and referenced generally by numeral 100. E/P system 100 includes components that must be mounted in/on seat 14, components that can be mounted on or coupled to either of seat 14 or base 12, and components that must be located remotely with respect to car seat 10. Such mounting and location will be described in detail below.

With respect to components mounted in/on seat 14, one or more microphones 102 are fitted in/on seat 14 near the seat's headrest area designated by area 20 in FIG. 1. For reasons that will be explained further below, at least two audio speakers 104A and 104B are fitted into or on headrest area 20. The particular placement of microphone(s) 102 and speakers 104A and 104B in headrest area 20 is not a limitation of the present invention. An electro-mechanical vibrating device 106 can optionally be provided and coupled to either back area 22 or seat area 24 (FIG. 1) of seat 14. When activated, vibrating device 106 introduces vibrational waves into seat 14 thereby making seat 14 vibrate in a massaging or soothing fashion. Such massage may pacify the child in seat 14. Again, the particular placement of such vibrating device 106 is not a limitation of the present invention. Also mounted on seat 14 are a plurality of child-controlled switches 120 which will be explained further below.

Mounted to either base 12 or seat 14 are the components for controlling speakers 104A/104B and vibrating device 106, and for receiving/using the outputs generated by microphone(s) 102. The components mounted in base 12 (or mounted to seat 14) include a plurality of audio sources 110, an anti-noise source 112, an audio electronics and amplification module 114, a switch controller 116, and a power management module 118. The advantage of mounting these components on seat 14 is that E/P system 100 can be utilized even when seat 14 is not mounted to base 12. The disadvantage is the weight that these components add to seat 14. Thus, if weight is a concern, it may be desirable to mount some or all of these components in base 12. However, this requires the use of connectors that would allow the coupling of these components to microphone(s) 102, speakers 104A/104B and vibrating device 106. Such connectors would ideally be automatically coupled upon the locking of seat 14 to base 12.

Audio sources 110 can include, for example, a white noise generator 110A, a music generator 110B and a human heartbeat simulation generator 110C. Each of these types of audio sources are well known in the art and can be realized in a variety of ways. For example, music generator 110B can be any one of a variety of digital type devices to include an MP3 player, a CD player, etc. White noise generator 110A can be used to generate a white noise signal having a spectral frequency distribution that is tuned/filtered to produce an audio output that is calming to the child in seat 14. Human heartbeat simulation generator 110C produces an audio signal that, when amplified, produced an audio output simulating a human heartbeat.

When activated, the audio signal produced by each of these sources can be filtered and amplified as needed by audio electronics and amplification module 114 before being supplied to at least one of speakers 104A. At any given time, only one of audio sources 110 is activated by switch controller 116 with the generated audio signal being reproduced at speakers 104A. Power for the selected one of audio sources 110 is supplied by power management module 118 which will be described later below.

Anti-noise source 112 is an active ambient noise suppression system that uses the output of microphone(s) 102 (i.e., the ambient noise detected in headrest area 20) to generate a (canceling) audio signal that is equal in magnitude but opposite in phase to the detected ambient noise. Such anti-noise suppression systems are well known in the art of broadcasting and airline pilot headsets. The anti-noise or canceling audio signal is filtered/amplified at module 114 before being reproduced at one or more of speakers 104B. Thus, at any given time, speakers 104A are dedicated to one of audio sources 110 while speakers 104B are dedicated to anti-noise source 112. Alternatively, the canceling audio signal (from source 112) can be blended with the audio signal (from a selected source 110) and fed to any or all of speakers 104A and 104B. In either case, the selected one of audio sources 110 is played in an environment (i.e., headrest area 20) that is free from outside ambient noise which can distract and/or overstimulate the child in seat 14. Note that since it is desired to cancel outside ambient noise (e.g., car noise, road noise, traffic noise, passenger conversation noise, etc.) while maintaining the audio produced by one of audio sources 110, microphone(s) 102 mounted in headrest area 20 may be directionally focused to detect ambient noise without detecting that generated by the selected one of audio sources 110.

Figure 3:
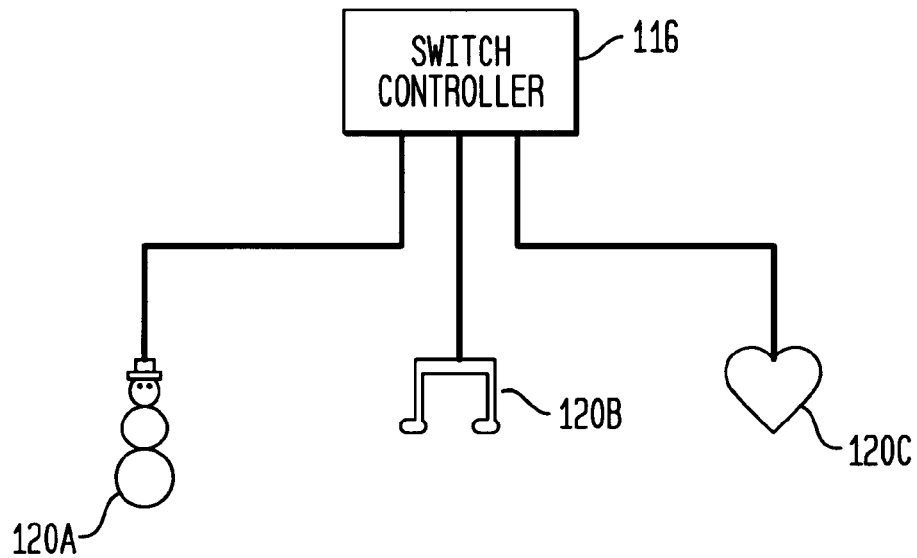
FIG. 3 depicts squeezable toy switches that can be used by the child in the car seat to control the audio sources in the entertainment and pacification system.

As previously mentioned, switch controller 116 is used to select which of audio sources 110 is activated, whether or not anti-noise source 112 is activated and, if included, whether or not vibrating device 106 is activated. Switch inputs can be provided the child in seat 14 by means of a plurality of manually-operated switches 120. For example, in the illustrated example, switches controlling audio sources 110 can be realized by squeezable bulb switches 120A, 120B and 120C that are in the shape of toy figures as illustrated in FIG. 3. Specifically, switch 120A in the, shape of a snowman is used to activate white noise generator 110, switch 120B in the shape of a musical note is used to activate music generator 110B, and switch 120C in the shape of a heart is used to activate human heartbeat simulation generator 110C. Additional toy switches would be provided for anti-noise source 112 and vibrating device 106.

Since some very young children may either not have the dexterity to work switches 120 or may become frustrated at not being able to get what they want, a second set of parent/driver controlled override switches 122 are also coupled to switch controller 116. Selection made at override switches 122 will take priority over any selections made by the child using switches 120. Switches 122 would typically be located remotely with respect to child car seat 10. Preferably; switches 122 are positioned such that a driver can make selections while driving.

Figure 4:
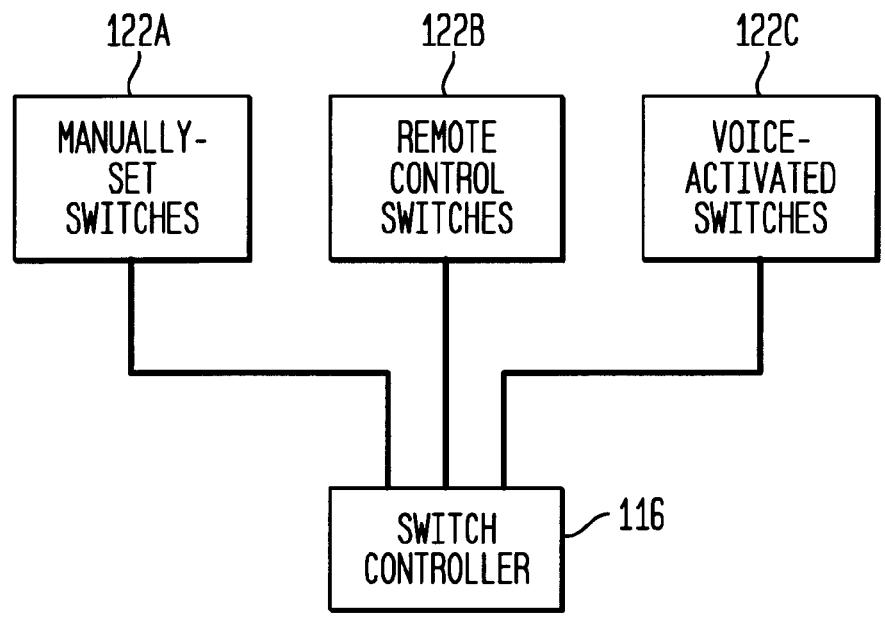
FIG. 4 is a schematic view of possible types of parent/driver override switches that can be used in the present invention.

Override switches 122 allow the parent/driver to select the particular one of audio sources 110 that keeps the child satisfied. Additionally or alternatively, override switches 122 allow the parent/driver to activate/deactivate anti-noise source 112 as needed and/or activate/deactivate vibrating device 106 as needed. As shown in FIG. 4, switches 122 could be manually-set switches 122A that are beyond the child's reach, remote control (e.g., an infrared or RF remote) switches 122B or voice-activated switches 122C. If either remote control switches 122B or voice-activated switches 122C are wireless-based, a wireless receiver 124 is coupled to switch controller 116.

Power management module 118 supplies power to components of E/P system 100 that are mounted on/in car seat 10. Such power can come "locally" from an onboard battery, or can come from a remotely located source such as the vehicle's battery (via the vehicle's cigarette lighter) or a standard 120 VAC source if E/P system 100 is to be used in a house or other building. Accordingly, power management module 118 typically includes means for receiving an outside power source (e.g., ports) and monitoring the particular source of power and converting/filtering/amplifying it to satisfy the requirements of the components of E/P system 100. Such power management controllers are well known in the art.

In operation, with a child in seat 14, the child can select one of audio sources 110, and the independent activation/deactivation of each of anti-noise source 112 and vibrating device 106. Provided the child is content with his/her choices, the parent/driver need not use override switches 122. However if the child is dissatisfied or unable to make selections, the parent/driver makes override selections using switches 122.

Figure 5:
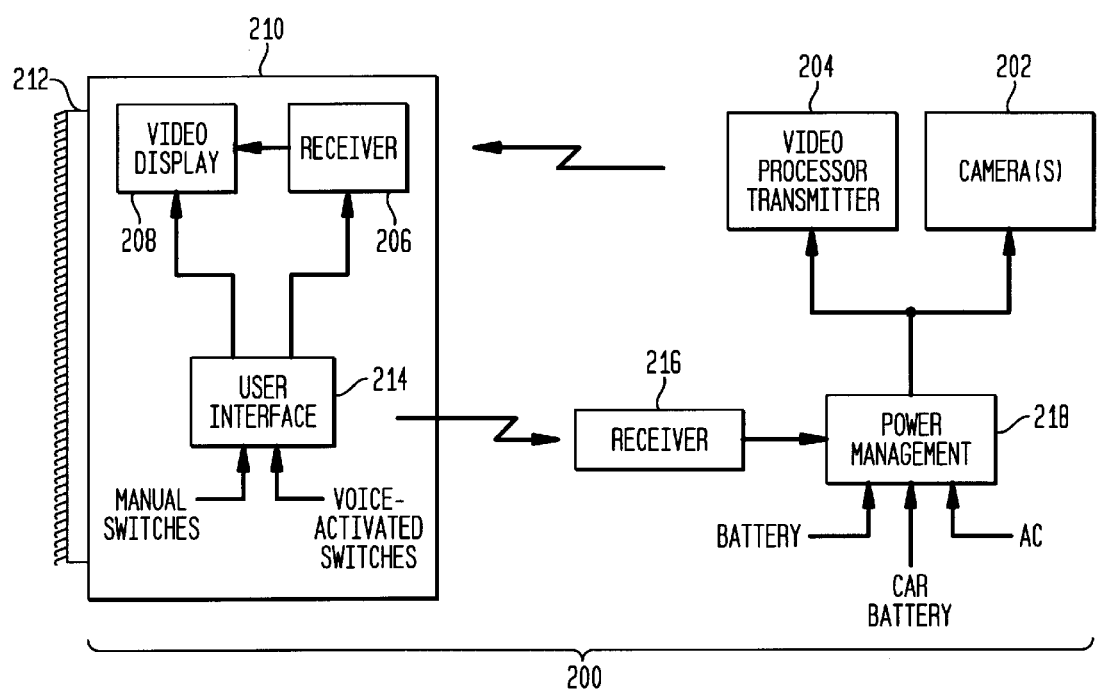
FIG. 5 is a schematic view of a video monitoring system that can be used to monitor a child in the car seat.

In addition to or as an alternative to E/P system 100, car seat 10 can be equipped with a video monitoring system 200 illustrated schematically in FIG. 5. Video monitoring system 200 includes components mounted in/on car seat 10 as well as components located remotely with respect to car seat 10. Mounted in or on seat 14 are one or more miniature video cameras 202 that can be mounted in headrest area 20 and/or on pull down handle 16 (FIG. 1). One or more of camera(s) 202 can be an infrared camera thereby allowing their use in low light or dark conditions without visible illumination which might disturb the child and/or distract the driver. If necessary, an infrared illuminator (not shown) can be included to insure satisfactory illumination regardless of ambient lighting conditions without disturbing the occupant of the car seat.

When activated, the video signal generated by camera(s) 202 is processed and transmitted wirelessly by means of a video processor/transmitter 204. Power for camera(s) 202 and processor/transmitter 204 can be supplied by a power management module 218 which is identical in concept to power management module 118. Accordingly, module 218 will not be discussed further herein.

Components located remotely with respect to car seat 10 include a wireless receiver 206 and a video display 208. Receiver 206 detects the transmitted video signals and presents same to video display 208 (e.g., an LCD or other lightweight display). Preferably, receiver 206 and video display 208 are encased in a portable housing 210 which can be easily placed/mounted in the front seat area of the vehicle in which car seat 10 is installed. For example, housing 210 could simply have a hook-and-loop fastening strip 212 coupled thereto for mating with a complementary strip (not shown) positioned where desired in the vehicle. The portable nature of housing 210 and its components allows system 200 to function in venues other than a vehicle when seat 14 is removed therefrom.

Activation and control of camera(s) 202, transmitter 204, receiver 206 and video display 208 can be provided by a user interface 214 which can be incorporated into housing 210. User interface 214 can include remote control features that issue wireless remote control signals to a receiver 216 at car seat 10 which can instruct power management module 218 to power the appropriate components. Such control signals are provided by the parent/driver using manually-generated switches and/or voice-activated switches supported by user interface 214.

Figure 6:
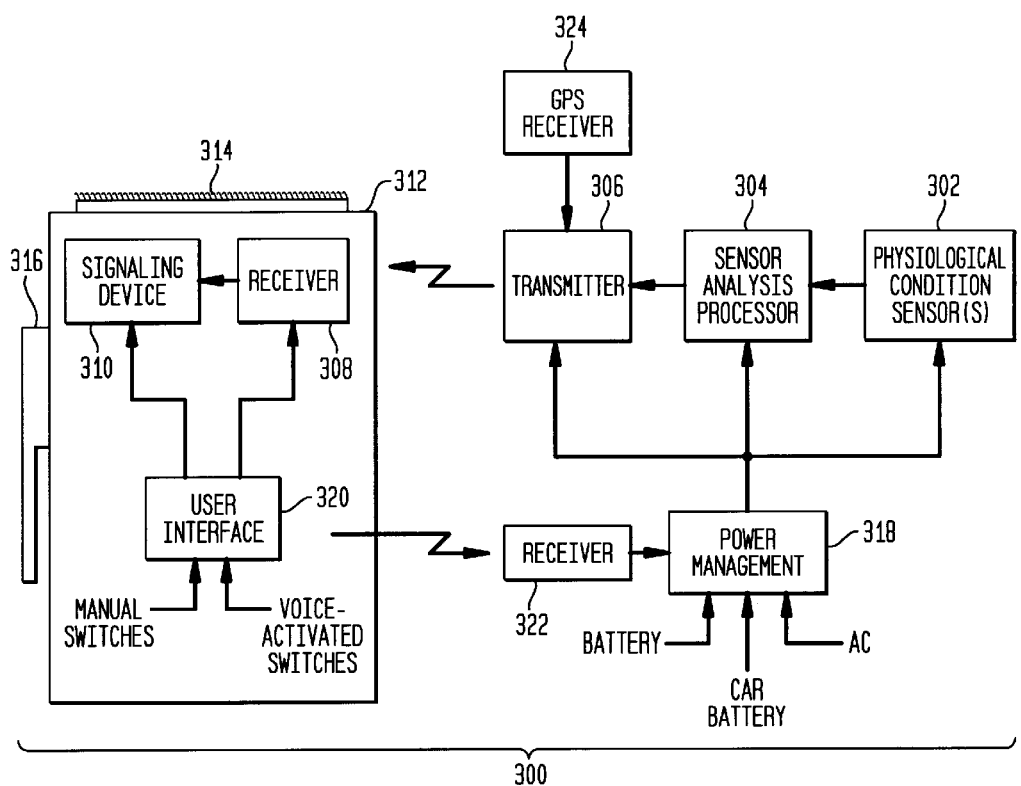
FIG. 6 is a schematic view of a health monitoring system that can be used to monitor a child in the car seat.

In addition to, or as an alternative to E/P system 100 and/or video monitoring system 200, car seat 10 can be equipped with a health monitoring system 300 which is illustrated schematically in FIG. 6. As with the above-described features, health monitoring system 300 includes components in/on car seat 10 as well as components located remotely with respect to car seat 10. More specifically, mounted in or on seat 14 are one or more physiological condition sensor(s) 302, a sensor analysis processor 304, a transmitter 306 and a power management module 318 which is identical in concept to power management module 118. With respect to sensor(s) 302, their particular mounting location depends on the type of sensor(s) and the condition being monitored. For example, in terms of a child's respiratory rate and heart rate, sensor(s) 302 could be one or more microphones located in the upper portion of back area 22 illustrated in FIG. 1. That is, such microphones would function much like a doctor's stethoscope pick-up head. Sensor(s) 302 could also include sensor(s) for measuring body temperature such as an infrared thermometer or pyrometer mounted, preferably, in headrest area 20 since such sensors need to access exposed skin, i.e., the child's face.

Sensor(s) 302 provide their sensed outputs to sensor analysis processor 304 where the sensed signals are compared with either known normal/abnormal levels or ranges thereof. For example, processor 304 might be programmed with acceptable/unacceptable thresholds or ranges for respiratory rates, heart rates and body temperatures. Note that these thresholds could be set to standard levels or specific levels if a child had special needs or concerns.

The results of the comparisons made a processor 304 would be used to generate a status signal which could be an actual reading, an "OK" or "not OK" status, or simply generate an alarm type of status signal only when a "not OK" condition exists. The status signals are passed to wireless transmitter 306 which transmits same over the air waves. Power for each of sensor(s) 302 (if needed), processor 304 and transmitter 306 can be supplied by power management module 318.

Components located remotely with respect to car seat 10 include a wireless receiver 308 and a signaling device 310. Receiver 308 detects the transmitted status signals and presents same to signaling device 310 which produces one or more outputs that can be easily monitored by the parent/driver. Accordingly, such outputs can be audible, visual or tactile in nature (e.g., vibration). Preferably, receiver 308 and signaling device 310 are encased in a portable housing 312 which can either be placed/mounted in the vehicle or worn on the parent/driver's clothing. For example, housing 312 can have a hook-and-loop fastening strip 314 coupled thereto and/or a belt clip 316 coupled thereto. The portable nature of housing 312 and its components allows system 300 to function in venues other than a vehicle when seat 14 is removed therefrom.

Activation and control of sensor(s) 302, processor 304, transmitter 306, receiver 308 and signaling device 310 can be provided by a user interface 320 which can be incorporated into housing 312. User interface 320 can include remote control features that issue wireless remote control signals to a receiver 322 at car seat 10 which can then pass such instructions to power management module 318 to power the appropriate components. Such control signals are provided by the parent/driver using manually-operated switches and/or voice activated switches.

Health monitoring system 300 can also include a tracking feature to allow the whereabouts of seat 14 to be monitored. Such tracking could be provided by GPS position signals received at a GPS receiver 324 mounted to seat 14. The GPS position signals could be passed to transmitter 306 for transmission over the airwaves.

The advantages of the present invention are numerous. A child in a car seat can now be entertained, pacified, monitored visually and/or monitored in terms of biological vital signs. All of the features can be controlled/monitored by the parent/driver without ever having to turn around and look into the back seat of the vehicle. Thus, the present invention provides a new level of vehicle safety for everyone on the road.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A health monitoring system for use with a child car seat, comprising:

sensors mounted in a child car seat for monitoring an occupant sitting therein in terms of at least one of respiratory rate, heart rate and body temperature of the occupant, and for generating signals indicative thereof;

a processor mounted to the child car seat and coupled to said sensors for monitoring said signals and for generating status signals related to at least one of respiratory rate, heart rate and body temperature of the occupant;

a transmitter mounted to the child car seat and coupled to said processor for wirelessly transmitting said status signals;

means for remotely controlling activation of said sensors, said processor and said transmitter;

a receiver located remotely with respect to the child car seat for receiving said status signals so-transmitted; and a signaling device coupled to said receiver for producing at least one sensory output based on said status signals, said at least one sensory output selected from the group consisting of visual, audible and tactile outputs.

2. A health monitoring system as in claim 1 wherein said means for remotely controlling is voice activated.

3. A health monitoring system as in claim 1 wherein said signaling device includes means for facilitating mounting of same in a vehicle in which the child car seat is installed.

4. A health monitoring system as in claim 1 wherein said signaling device includes means for attaching same to an article of clothing.

5. A health monitoring system as in claim 1 further comprising a GPS receiver mounted to the child car seat for sensing a position of the child car seat and for generating a position signal indicative thereof, said GPS receiver coupled to said transmitter wherein said position signal is transmitted wirelessly therefrom.

6. A health monitoring system as in claim 1 wherein said processor is programmed with at least one threshold level of respiratory rate, heart rate and body temperature, and wherein said status signals are based on relationships between said signals so-monitored and said at least one threshold.

7. A health monitoring system for use with a child car seat, comprising:

sensors mounted in a child car seat for monitoring an occupant sitting therein in terms of at least one of respiratory rate, heart rate and body temperature of the occupant, and for generating signals indicative thereof;

a processor mounted to the child car seat and coupled to said sensors for monitoring said signals and for generating status signals related to at least one of respiratory rate, heart rate and body temperature of the occupant;

a transmitter mounted to the child car seat and coupled to said processor for wirelessly transmitting said status signals;

means for remotely controlling activation of said sensors, said processor and said transmitter;

power management means mounted on the child car seat and coupled to said sensors, said processor and said transmitter for supplying power thereto, said power management means including a rechargeable battery serving as a local source of said power and at least one port for receiving said power from a remotely-located source of said power;

a receiver located remotely with respect to the child car seat for receiving said status signals so-transmitted; and a signaling device coupled to said receiver for producing at least one sensory output based on said status signals, said at least one sensory output selected from the group consisting of visual, audible and tactile outputs.

8. A health monitoring system as in claim 7 wherein said means for remotely controlling is voice activated.

9. A health monitoring system as in claim 7 wherein said signaling device includes means for facilitating mounting of same in a vehicle in which the child car seat is installed.

10. A health monitoring system as in claim 7 wherein said signaling device includes means for attaching same to an article of clothing.

11. A health monitoring system as in claim 7 further comprising a GPS receiver mounted to the child car seat for sensing a position of the child car seat and for generating a position signal indicative thereof, said GPS receiver coupled to said transmitter wherein said position signal is transmitted wirelessly therefrom.

12. A health monitoring system as in claim 7 wherein said processor is programmed with at least one threshold level of respiratory rate, heart rate and body temperature, and wherein said status signals are based on relationships between said signals so-monitored and said at least one threshold.

* * * * *